(12) United States Patent
Rayner-Brandes et al.

(10) Patent No.: US 9,399,757 B2
(45) Date of Patent: Jul. 26, 2016

(54) DRY GRANULATED CELL CULTURE MEDIA

(75) Inventors: Michael Howard Rayner-Brandes, Seeheim-Jugenheim (DE); Xiaojian (David) Zhao, Clarence, NY (US)

(73) Assignee: MERCK PATENT GMBH, Darmstadt (DE)

( * ) Notice: Subject to any disclaimer, the term of this patent is extended or adjusted under 35 U.S.C. 154(b) by 80 days.

(21) Appl. No.: 13/994,239

(22) PCT Filed: Nov. 18, 2011

(86) PCT No.: PCT/EP2011/005830
§ 371 (c)(1),
(2), (4) Date: Jun. 14, 2013

(87) PCT Pub. No.: WO2012/079679
PCT Pub. Date: Jun. 21, 2012

(65) Prior Publication Data
US 2013/0267027 A1    Oct. 10, 2013

Related U.S. Application Data

(60) Provisional application No. 61/423,700, filed on Dec. 16, 2010.

(51) Int. Cl.
*C12N 5/00* (2006.01)
(52) U.S. Cl.
CPC ............ *C12N 5/0043* (2013.01); *C12N 5/0018* (2013.01)

(58) Field of Classification Search
None
See application file for complete search history.

(56) References Cited

U.S. PATENT DOCUMENTS

| 6,383,810 B2 | 5/2002 | Fike et al. |
| 2006/0275886 A1 | 12/2006 | Fike et al. |
| 2008/0019883 A1 | 1/2008 | Fike et al. |
| 2008/0254119 A1 | 10/2008 | Dai et al. |
| 2008/0261308 A1 | 10/2008 | Fike et al. |
| 2008/0311660 A1 | 12/2008 | Fike et al. |
| 2011/0129926 A1 | 6/2011 | Fike et al. |
| 2013/0109094 A1 | 5/2013 | Fike et al. |

FOREIGN PATENT DOCUMENTS

| WO | 02/36735 A2 | 5/2002 |
| WO | WO 2008074015 A1 * | 6/2008 |

OTHER PUBLICATIONS

Fike et al. "Advanced granulation technology (AGT™): An alternate format for serum-free, chemically-defined and protein-free cell culture media", Cytotechnology 36: 33-39, 2001.*
Wennerstrum "Ten things you need to consider when choosing and installing a roller press system", Powder and Bulk Engineering Feb. 2000.*
Kleinebudde "Roll compaction/dry granulation: pharmaceutical applications", European Journal of Pharmaceutics and Biopharmaceutics 58(2): 317-326, 2004.*
International Search Report for PCT/EP2011/005830 (Jan. 20, 2012).
R. Fike et al., "Advanced Granulation Technology (AGTTM)—An Alternate Format for Serum-Free, Chemically-Defined and Protein-Free Cell Culture Media", Cytotechnolgy, vol. 36, No. 1-3 (Jul. 2001) pp. 33-39.

* cited by examiner

*Primary Examiner* — Emily Cordas
(74) *Attorney, Agent, or Firm* — Millen White Zelano and Branigan, PC; John Sopp; Anthony Zelano

(57) ABSTRACT

The present invention relates dry granulated cell culture media which do not comprise peptones or tryptones, especially to dry granulated cell culture media formulations that support the growth of mammalian, and/or insect and/or plant cells. The present invention further relates to the production of these dry granulated cell culture media and their use.

7 Claims, 1 Drawing Sheet

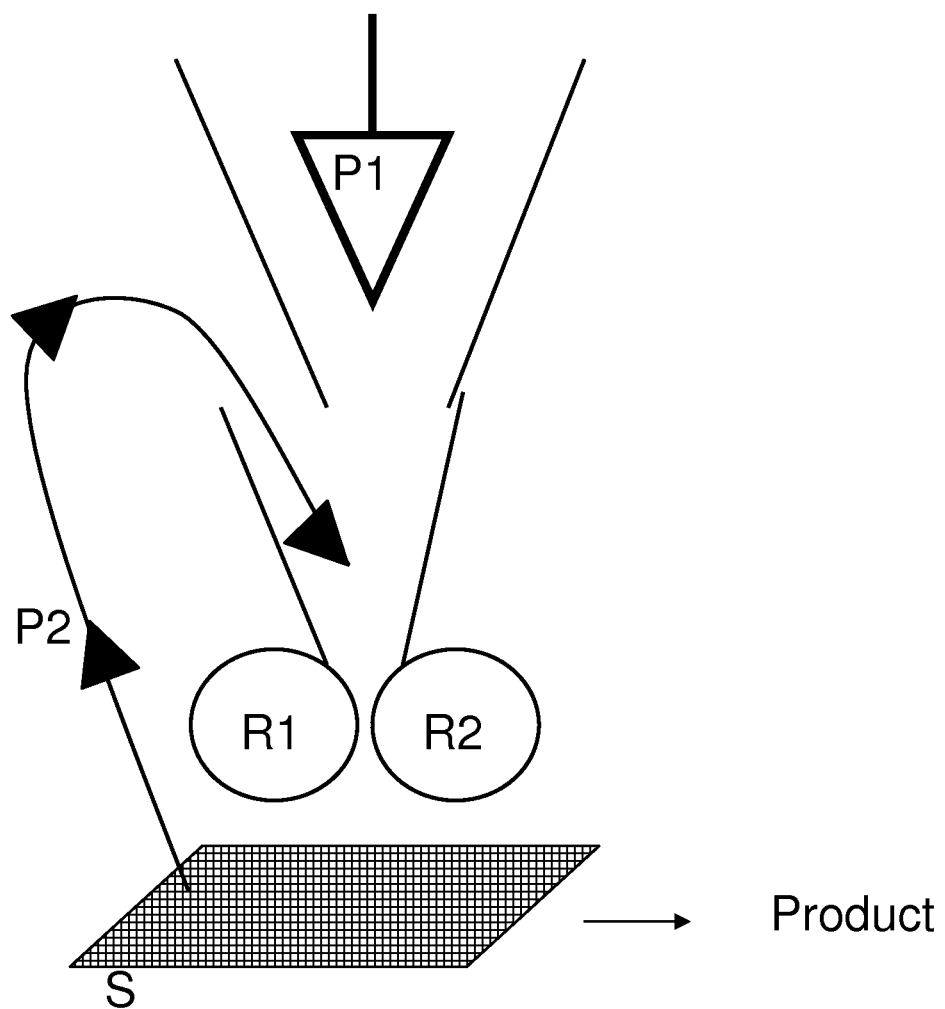

DRY GRANULATED CELL CULTURE MEDIA

The present invention relates to dry granulated cell culture media which do not comprise peptones or tryptones, especially to dry granulated cell culture media formulations that support the growth of mammalian, and/or insect and/or plant cells. The present invention further relates to the production of these dry granulated cell culture media and their use.

BACKGROUND OF THE INVENTION

Cell culture media support and maintain the growth of cells in an artificial environment.

Depending on the type of organism whose growth shall be supported, the cell culture media may comprise more than 10, sometimes more than one hundred different components.

The culture media required for the propagation of mammalian, insect or plant cells are typically much more complex than the minimal media sufficient to support the growth of bacteria and yeasts.

Early studies of cell culture utilized media consisting of undefined components, such as plasma, serum, embryo extracts, other non-defined biological extracts or peptones. A major advance was thus made with the development of chemically defined media. Chemically defined media often comprise but are not exclusively limited to amino acids, vitamins, metal ions, antioxidants, chelators, growth factors, buffers, hormones, chlorides and many more substances known to those expert in the art Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. They are manufactured for the purpose of dissolving in water and/or aqueous solutions and in the dissolved state are designed, often with other supplements, for supplying biological cells with a substantial nutrient base for growth and/or production of biopharmaceuticals from same said cells.

The handling of finely milled powders has significant disadvantages. For example, they are very dusty to handle, more so in large amounts, which can lead to health problems of workers handling the material especially if some of the individual raw materials are hazardous to health. Even if the individual components are not directly toxic there can be health problems caused to workers by high dust levels in the breathable air per se and amounts of dust in air are strictly regulated in many countries due to this problem. Furthermore dust of organic materials, more especially fine dust, can easily result in explosions if amounts are excessive and cautionary measures are not adequate to prevent ignition by sparks.

In addition, it can occur under disadvantageous transport conditions, for example during long transport conditions, that one or more of the lighter individual components of the dry powder media migrates towards the surface or one or more heavier components migrates towards the base of the primary packaging. The result of this local higher concentration or, in the physical centre of the bulk material, the depletion of certain individual component/s, can be negative in many ways on the product quality of the media. In addition, the de-mixing can have effects far beyond physical depletion and concentration of individual components, for example, on target biopharmaceutical molecule production amounts per batch or more subtly on the oligosaccharide patterning on biopharmaceuticals themselves making media quality absolutely critical to biopharmaceutical quality right until the patient.

Another aspect when using finely milled dry powder media is the difficulty to dissolve the fine powder in aqueous solutions to prepare the final aqueous cell culture medium. It is very difficult to wet a finely milled powder and dissolve it in an aqueous liquid. Therefore, the handling of the powder media and their use is quite complicated.

Due to the limitation of dry power media for stability, mixing and dissolving, media in dry format are usually produced without some key supplements such as carbonate, hydrolysates, growth factors and other trace elements, which end users will supplement when they prepare liquid from the dry powder media. The additional handling and supplementing will increase the potential for very costive errors and labour.

It is known that powdered bacterial cell culture media can be granulated by pressing the powder to small granules. The result are small particles with advantages in safety, handling and performance. This procedure can be easily realized for bacterial cell culture media as they comprise chemically poorly defined peptones or tryptones or equivalent peptidic components that support the adherence of the media components through their inherent stickiness.

Mammalian, and/or insect and/or plant cell culture media typically do not contain peptones or their equivalents and are thus much more difficult to handle in this manner.

U.S. Pat. No. 6,383,810 B2 by Invitrogen Corporation discloses a method of producing an agglomerated eukaryotic cell culture medium powder. The method comprises wetting a dry powder cell culture medium with a solvent and then re-drying the moistened medium to obtain a dry agglomerated cell culture medium.

A great disadvantage of this procedure is the fact that the whole medium components need to be contacted with water and that they need to be heated to remove the water afterwards. This may cause considerable side reactions among the components of the medium or destruction or modification of sensitive components with an unpredictable outcome on the medium quality.

Consequently, there exists a clear need for finding a new form of mammalian, and/or insect and/or plant cell culture media which is easy to handle and can be produced without causing destruction and/or side reactions among the medium components.

BRIEF DESCRIPTION OF THE INVENTION

It has been found that also peptone free, chemically defined mammalian, and/or insect and/or plant cell culture media can be produced in a dry granulated form by compacting the mixed, finely milled powder of the dry medium components. Compaction is achieved by press agglomeration in role presses. No additives need to be used to aid the process. The dry granulated cell culture media according to the present invention have a long shelf life, are easy to handle and are produced under very mild conditions so that no side reactions occur due to wetting or heating the medium components during the manufacturing process.

Therefore the present invention relates to a method for producing a dry granulated cell culture medium which does not comprise peptones or tryptones by
   a) providing a cell culture medium in form of a mixed powder of the medium components, whereby the mixed powder does not comprise peptones or tryptones
   b) compacting said mixed powder in a roll press In a preferred embodiment the cell culture medium that is provided in step a) is a mammalian cell culture medium.

In a preferred embodiment the cell culture medium that is provided in step a) comprises one or more saccharide components, one or more amino acids, one or more vitamins, one or more salts, one or more buffer components, one or more co-factors and one or more nucleic acid components.

In a very preferred embodiment, step b) is performed by b1) compacting said mixed powder in a roll press b2) reintroducing all parts of the compacted cell culture medium obtained in step b1) which have a particle size of smaller than 0.2 mm into the cell culture medium in form of a mixed powder of the medium components to be filled in the roll press.

In a preferred embodiment, the press capacity of the roll press is between 30 and 80 kN/cm roll width.

The present invention is further directed to a dry granulated cell culture medium which does not comprise peptones or tryptones that can be prepared according to the method according to the present invention. In a preferred embodiment, more than 80% of the particles of the granulated cell culture medium have a size larger than 0.5 mm.

In a very preferred embodiment, more than 90% of the particles of the granulated cell culture medium have a size larger than 0.5 mm.

In another preferred embodiment, the dry granulated cell culture medium which does not comprise peptones or tryptones is a chemically defined mammalian cell culture medium.

In another preferred embodiment, the dry granulated cell culture medium which does not comprise peptones or tryptones comprises one or more saccharide components, one or more amino acids, one or more vitamins, one or more salts, one or more buffer components, one or more co-factors and one or more nucleic acid components.

The present invention is further directed to the use of a dry granulated cell culture medium which does not comprise peptones or tryptones for culturing cells according to the present invention by:

a) dissolving the dry granulated cell culture medium which does not comprise peptones or tryptones in a solvent to form a liquid cell culture medium b) contacting said liquid cell culture medium with said cells to be cultured In a preferred embodiment said cells to be cultured are mammalian cells.

In a preferred embodiment the solvent in step a) is water.

In addition to the above mentioned single embodiments and aspects of the present invention, the present invention can also be realized and put into practice in every combination of two or more of the disclosed embodiments or aspects.

DESCRIPTION OF THE INVENTION

FIG. 1 shows a schematic view of a dry compaction equipment suitable for the present invention.

Dry granulation according to the present invention creates granules or particles by compaction of the powders under pressure—without the addition of water or other solvents. Typically, the roll press which is used according to the present invention generates also larger compacts or flakes. These compacts so-formed are typically broken up gently, e.g. by a vibrating sieve, to produce granulated particles (agglomerates). According to the present invention a powder or a finely milled powder is a composition of particles of which more than 80% have a particle size (diameter) of less than 0.2 mm. Preferably, the powder is dry and free-flowing. With the expression "free flowing powder" is meant a powder (made by milling, micropelletizing or similar technique) of which the particles do not adhere to one another. All powders that show an angle of repose below about 50 degrees typically show suitable flow properties but as used herein, the terms dry and free-flowing shall also refer to the gross appearance of the powder—that means the powder looks dry and free-flowing.

A cell culture medium according to the present invention is any mixture of components which maintains and/or supports the in vitro growth of cells. The cell culture medium can comprise all components necessary to maintain and/or support the in vitro growth of cells or only some components so that further components are added separately. Examples of cell culture media according to the present invention are full media which comprise all components necessary to maintain and/or support the in vitro growth of cells, media supplements or feeds. In a preferred embodiment the cell culture medium is a full medium.

Typically the cell culture media according to the invention are used to maintain and/or support the growth of cells in a bioreactor.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells.

Cells to be cultured with the media according to the present invention may be normal cells, diseased cells, transformed cells, mutant cells, somatic cells, germ cells, stem cells, precursor cells or embryonic cells, any of which may be established or transformed cell lines or obtained from natural sources.

A cell culture medium which does not comprise peptones or tryptones is a cell culture medium which does not contain any peptones or tryptones or other peptides produced by partial hydrolysis of proteins.

In a preferred embodiment the cell culture medium which does no comprise peptones or tryptones also does not comprise any proteins or other naturally derived polymers like agar. In a very preferred embodiment, the cell culture medium which does not comprise peptones or tryptones is a chemically defined cell culture medium.

Chemically defined cell culture media are cell culture media which do not comprise any chemically undefined substances. That means the chemical composition and structure of all the chemicals used in the chemically defined media are known. The chemically defined media do not comprise any yeast, animal or plant tissue; they do not comprise feeder cells, serum, extracts or digests or other components which may contribute chemically poorly defined proteins to the media. Chemically undefined or poorly defined chemical structures are those whose chemical composition and structure is not known or could only be defined with enormous experimental effort—comparable to the evaluation of the chemical composition and structure of a protein like albumine or casein.

In one embodiment, the cell culture medium which does not comprise peptones or tryptones according to the invention only contains one or more saccharide components, one or more amino acids, one or more vitamins, one or more salts, one or more buffer components, one or more co-factors and one or more nucleic acid components.

The size of a particle means the mean diameter of the particle. The particle diameter is determined by laser light scattering in silicone oil.

Saccharide components are all mono- or di-saccharides, like glucose, galactose, ribose or fructose (examples of monosaccharides) or sucrose, lactose or maltose (examples of disaccharides).

Examples of amino acids according to the invention are the proteinogenic amino acids, especially the essential amino acids, leucine, isoleucine, lysine, methionine, phenylalanine, threonine, tryptophane and valine, as well as the non-proteinogenic amino acids like D-amino acids.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn.

Examples of buffers are $CO_2/HCO_3$, HEPES, PIPES, ACES, BES, TES, MOPS and TRIS.

Examples of cofactors are thiamine derivatives, biotin, vitamin C, NAD/NADP, cobalamin, flavin mononucleotide and derivatives, glutathione, heme nucleotide phophates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

A stable cell culture medium is a medium which after storage over a certain amount of time shows at least 80% preferably at least 90%, more preferred at least 97%, most preferred the same biological and biochemical activity when compared to a freshly made medium of the same formulation.

The present invention is based on the finding that also media which do not comprise peptones or tryptones or similar components can be provided in a dry granulated form. This was very unexpected as up to now only cell culture media with peptones or tryptones could be dry granulated. It was assumed that the adhesive properties of the peptones or tryptones were essential for the production of dry granulated media.

It has been found that a special compaction procedure also enables the production of dry granulated media which do not comprise peptones or tryptones.

The compaction procedure according to the present invention is performed in two basic steps.

a) providing a cell culture medium in form of a mixed powder of the medium components b) compacting said mixed powder in a roll press In step a), a finely milled dry powder of the media components is provided. All components are thoroughly mixed so that all parts of the powder mixture have nearly the same composition. The mixture should have the same quality with respect to its uniformity of composition as a commercial dry powder cell culture medium. The higher the uniformity of the composition, the better the quality of the resulting dry granulated medium with respect to homogenous cell growth. Mills which are suitable to produce fine milled powders are for example ball mills, pin mills, jet mills or rotating blade sieve mills. The particle size of the powders is typically below 500 µm, preferably below 200 µm.

To provide a mixed powder of the medium components the components can for example be first mixed and then finely milled as a mixture or they can be milled separately or in sub-groups and combined and mixed afterwards.

Preferably all components of the mixture are dry. That means, if they comprise water, they do only comprise water of crystallization but not more than 5%, preferably not more than 2% most preferred not more than 1% by weight of unbound or uncoordinated water molecules.

If one or more of the mixture components is sensitive to oxidation, the mixing and milling can be performed under an inert protective gas.

In the second step, step b), the powder mixture is compacted in a roll press.

A roll press, also called roller compactor, is known to a person skilled in the art. Typically a roll press comprises two counter-rotating rolls which are located at a small distance of about 0.5 to 3 mm, preferably 1 to 2 mm next to each other. Suitable roll presses typically have rolls with a widths between 10 and 50 cm resulting in the gap between the roll having a length between 10 and 50 cm. Nevertheless, the size of the rolls and thus the length of the gap between the rolls can vary depending on the size of the roll press. In a preferred embodiment, the gap has a length between 10 and 15 cm.

The mixed powder material is drawn in between the counter-rotating rolls and compacted in the gap between the rolls. The distance between the rolls and their surface structure have influence on the final size and structure of the resulting granulated particles.

The surface of the rolls is preferably riffled. The riffles help to make the powder stick to the roll and to pull it through the press.

The press capacity of the roll press typically is between 20 and 150 kN/cm roll width, preferably the rolls are pressed together with a force between 30 and 80 kN, most preferred between 40 and 60 kN.

If the components of the cell culture medium are very sensitive, the compacting procedure can be performed under an inert protective gas atmosphere. In addition, the rolls of the roll press are usually cooled to maintain a constant temperature since often some components are heat-sensitive and would not stand the slightly enlarged temperature which might occur due to compaction.

In a preferred embodiment, the compacted cell culture medium which is set free from the roll press is directly sized. This can for example be done by sieving, e.g. with one or more vibrating sieves. The diameter of the holes in the sieve depends on the size of the granules to be collected. For the process according to the present invention, a typical diameter is between 0.5 to 5 mm, preferably around 1 to 3 mm. Especially if the dry granulation in the roll press results in larger compacts or flakes, preferably, a sieve mill is used for granulating the compacts or flakes to granules of suitable size. One suitable sieve mill is the oscillating sieve mill, type FC 200, Bepex GmbH, with a sieve size between 1 and 3 mm.

Roll presses which are suitable for the process according to the present invention, can for example be purchased from Alexanderwerk, Sahut Coreur, Hosokawa or Fitzpatrick Company.

As already explained, the size of the particles of the dry granulated cell culture medium depends on the way the compacted medium which comes out of the roll press is treated. If the medium is directly collected from the roll press, it typically comprises larger compacts or flakes. If the medium is sieved, the particle size is determined by the size of the sieve.

But also further handling like packaging typically influences the mean particle size as some particles of the granulated cell culture media might break into pieces.

In a preferred embodiment, after compaction and sieving, more than 80% of the particles of the granulated cell culture medium have a size larger than 0.5 mm.

In a very preferred embodiment, more than 90% of the particles of the granulated cell culture medium have a size larger than 0.5 mm.

It has been found that the quality of the granulated cell culture media according to the invention can be further improved if the fraction of the compacted media which is set free from the roll press which has particle sizes smaller than 0.5, preferably smaller than 0.2 mm, is continuously reintroduced into the feed of the roll press again to be re-mixed with the powder mixture and to be re-pressed. This reduces the powder fraction of the final dry granulated cell culture medium and additionally improves the homogeneity of the product.

FIG. 1 gives a schematic view of one possible production assembly. The roll press is shown as roll R1 and roll R2. The powder mixture P1 is fed from a reservoir into the roll press. The compacted mixture which is set free from the roll press is sized with sieve S. The product fraction is removed for further treatment and packaging, the powder fraction P2 which has a particle size below 0.2 mm is continuously reintroduced into the feed of the roll press.

It has been found that the dry granulation according to the present invention can be performed without the addition of substances to enlarge the stickiness of the mixture.

The resulting dry granulated cell culture medium can then be further processed. The medium can be packaged and/or sterilized. Suitable containers are known to a person skilled in the art. Examples are bags, boxes, bottles, cartons, vacuum-packed forms etc. The packaging can be performed prior or after sterilization. Preferred is gamma-irradiation after appropriate packaging.

The dry granulated cell culture media according to the present invention can also favourably be used for the production of other compacted media forms like tablets or larger flakes. For this, the dry granulated cell culture media according to the present invention are subjected to further compaction in a suitable press, e.g. a tablet press. The granulated medium can be used as it is without the addition of other components or can be mixed with other components like tabletting aids or mixed or later on coated with components specific for e.g. slow release tablets. On the other hand the dry granulated cell culture medium can be mixed with components that support the fast dissolution of the tablets, like sodium bicarbonate.

The cell culture media which are dry granulated or compacted according to the method of the present invention typically comprise at least one or more saccharide components, one or more amino acids, one or more vitamins or vitamin precursors, one or more salts, one or more buffer components, one or more co-factors and one or more nucleic acid components.

The media may also comprise fatty acids and/or fatty acid derivatives and/or plutonic acid and/or surface active components like chemically prepared non-ionic surfactants, One example of a suitable non-ionic surfactant are difunctional block copolymer surfactants terminating in primary hydroxy groups, e.g. available under the trade name PLURONIC® from BASF, Germany.

The dry granulated media according to the present invention can be used for the same purposes as the powder media or liquid media known in the art. They can be preferably used in biopharma production as also large amounts of the granulated media can easily be handled without the disadvantages discussed for the powder media.

For use, a solvent, preferably water (most particularly distilled and/or deionized water or purified water or water for injection) or an aqueous buffer is added to the dry granulated media and the components are mixed until the medium is totally dissolved in the solvent.

The solvent may also comprise saline, soluble acid or base ions providing a pH range of 1.0-10.0, stabilizers, surfactants, preservatives, and alcohols or other polar organic solvents.

It is also possible to add further substances like buffer substances for adjustment of the pH, fetal calf serum, sugars etc., to the mixture of the cell culture medium and the solvent. The resulting liquid cell culture medium is then contacted with the cells to be grown or maintained.

The dry granulated media according to the present invention are easy to handle. In comparison to powder media, the amount of dust which forms when handling the media is significantly reduced.

The media according to the present invention can easily be dissolved in solvents. The reconstitution is rapid, preferably less than 30 minutes, more preferably less than 15 minutes.

The composition of the dry granulated media according to the present invention remains homogenous, even in case of shaking or vibration during transport.

In addition, in contrast to wet granulated media, the milder dry granulation conditions allow for the direct and easy processing of media comprising even heat- and/or oxidation sensitive substances like vitamins (e.g. vitamin B1), glucose, thiamine, iron salts or components comprising disulfide bonds.

The present invention is further illustrated by the following FIGURES and examples, however, without being restricted thereto.

The entire disclosures of all applications, patents, and publications cited above and below and of corresponding U.S. provisional application 61/423,700, filed Dec. 16, 2010, are hereby incorporated by reference.

Examples

The following examples represent practical applications of the invention.

1. Dry Compaction of Dulbecco's Modified Eagle Medium

Dulbecco's Modified Eagle Medium, also known as DMEM, is a medium often used for growing animal cells. The ingredients of DMEM are in mg/l:

Inorganic Salts:
$CaCl_2$ (waterfree): 200.00
$Fe(NO_3)_3.9H_2O$: 0.10
KCl: 400.00
$MgSO_4$ (waterfree): 97.67
NaCl: 6400.00
$NaH_2PO_4.H_2O$: 125.00
Other Components:
D-Glucose: 4500.00
Phenolred: 15.00
Natriumpyruvat: 110.00
Amino Acids:
L-Arginin HCl: 84.00
L-Cystine 2HCl: 63.00
L-Glutamine: 584.00
Glycine: 30.00
L-Histidine HCl $H_2O$: 42.00
L-Isoleucin: 105.00
L-Leucine: 105.00

L-Lysin HCl: 146.00
L-Methionine: 30.00
L-Phenylalanine: 66.00
L-Serine: 42.00
L-Threonine: 95.00
L-Tryptophane: 16.00
L-Tyrosine 2Na.2H$_2$O: 104.33
L-Valine: 94.00
Vitamins:
D-Calciumpantothenat: 4.00
Cholinchloride: 4.00
Folic acid: 4.00
i-Inositole: 7.20
Niacinamide: 4.00
Riboflavine: 0.40
Thiamine HCl: 4.00

All ingredients of the DMEM medium are mixed and milled in a pin mill to give a homogenous dry powder. 30 kg of the powder are fed into a roll press with the following characteristics:

concave plane rolls
distance between the rolls: 1.5 mm
length of the gap between the rolls: 10 cm
press force: 50 kN The resulting material shows a high percentage of larger compacts. The resulting material is sieved in an oscillating sieve mill, type FC 200, Bepex GmbH, with a sieve size of 3 mm.

The fraction of granules with a size (diameter) below 0.2 mm are reintroduced into the roll press. One obtains a dry granulated DMEM medium with more than 75% of the granules having sizes between 1 and 3 mm.

The invention claimed is:

1. A method for producing a dry granulated cell culture medium which does not comprise peptones or tryptones comprising:

a) providing a cell culture medium in the form of a mixed powder of the medium components, whereby the medium does not comprise peptones or tryptones; and b) filling said mixed powder in a roll press and compacting said mixed powder in said roll press, wherein the method is performed without the addition of water or other solvents.

2. A method according to claim 1, wherein the cell culture medium that is provided in step a) is a mammalian cell culture medium.

3. A method according to claim 1, wherein the cell culture medium that is provided in step a) comprises one or more saccharide components, one or more amino acids, one or more vitamins, one or more salts, one or more buffer components, one or more co-factors and one or more nucleic acid components.

4. A method according to claim 1, wherein step b) comprises:

b1) compacting said mixed powder in a roll press; and b2) reintroducing all parts of the compacted cell culture medium obtained in step b1) which have a particle size of smaller than 0.5 mm into the cell culture medium in the form of a mixed powder of the medium components to be filled in the roll press.

5. A method according to claim 1, wherein the press capacity of the roll press is between 30 and 80 kN/cm roll width.

6. A method according to claim 1, wherein the size of the gap between the rolls of the roll press is between 0.5 and 3 mm.

7. A method according to claim 1, wherein in a step c) the material obtained from step b) is further processed in a sieve mill.

* * * * *